United States Patent [19]

Kummer et al.

[11] Patent Number: 4,777,285
[45] Date of Patent: Oct. 11, 1988

[54] PREPARATION OF ALKENECARBOXYLATES

[75] Inventors: Rudolf Kummer, Frankenthal; Uwe Vagt, Speyer; Rolf Fischer, Heidelberg; Walter Seufert, Speyer; Rainer Becker, Bad Durkheim, all of Fed. Rep. of Germany

[73] Assignee: BASF Aktiengesellschaft, Ludwigshafen, Fed. Rep. of Germany

[21] Appl. No.: 28,135

[22] Filed: Mar. 19, 1987

[30] Foreign Application Priority Data

Mar. 19, 1986 [DE] Fed. Rep. of Germany ....... 3609138

[51] Int. Cl.⁴ .............................................. C07C 67/30
[52] U.S. Cl. .................................. 560/205; 260/405.5; 260/410.9 R; 502/202; 502/232; 502/240; 502/242; 502/263; 502/300; 502/350; 502/355; 560/211; 560/214; 562/599
[58] Field of Search ....................... 560/205, 211, 214; 562/599; 502/202, 232, 240, 242, 263, 300, 350, 355; 260/405.5, 410.9 R

[56] References Cited

U.S. PATENT DOCUMENTS 3,182,077 5/1965 Dever ................................. 560/205

OTHER PUBLICATIONS

Chemical Abstracts, vol. 82, No. 19; May 12, 1975, 124673j.
Nippon Nogeikagaku Kaishi, Dec. 1974, 48, pp. 525–527.

Primary Examiner—Werren B. Lone
Assistant Examiner—Vera C. Clarke
Attorney, Agent, or Firm—Keil & Weinkauf

[57] ABSTRACT

Alkenecarboxylates of the formula I

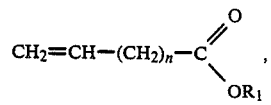

where $R_1$ is alkyl of 1 to 6 carbon atoms and n is 2, 3 or 4, are prepared by a process which comprises reacting a lactone of the formula II

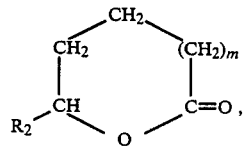

where $R_2$ is hydrogen or methyl and m is 1 or 2, with an alkanol of 1 to 6 carbon atoms in the presence of an acidic catalyst at from 150° to 400° C.

7 Claims, No Drawings

PREPARATION OF ALKENECARBOXYLATES

Nippon Nogei Kogaku Kaishi 48 (1974), 525–527 (C.A. 82, 124,673 (1975)) discloses that omega-hydroxycarboxylates are obtained by reacting 5-membered to 7-membered lactones with alcohols in the presence of magnesium alcoholates or acids.

It is an object of the present invention to provide a one-stage process for the preparation of alkenecarboxylates possessing a terminal double bond, starting from corresponding 6-membered or 7-membered lactones.

We have found that this object is achieved by a process for the preparation of alkenecarboxylates of the formula

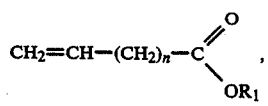

where $R_1$ is alkyl of 1 to 6 carbon atoms and n is 2, 3 or 4, by reacting a lactone of the formula II

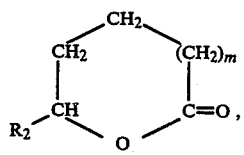

where $R_2$ is hydrogen or methyl and m is 1 or 2, with an alkanol of 1 to 6 carbon atoms in the presence of an acidic catalyst, wherein the reaction is carried out at from 150° to 400° C.

The novel process has the advantage that alkenecarboxylates possessing a terminal double bond are obtained in good yields in one stage, starting from 6-membered or 7-membered lactones. Another advantage of the novel process is that it can be carried out in a technically simple manner.

The novel process is noteworthy in that lactone cleavage to give alkenecarboxylates takes place in preference to ether formation from the participating alcohols, which is likewise acid-catalyzed, and the double bond is obtained in the terminal position despite the use of a catalyst.

According to the invention, lactones of the formula II are used as starting materials. Examples of suitable lactones are caprolactone, 7-methylcaprolactone, δ-valerolactone and 6-methylvalerolactone. Caprolactone, δ-valerolactone and 6-methylvalerolactone are preferred starting materials.

The reaction is carried out using alkanols of 1 to 6 carbon atoms. Examples of suitable alkanols are methanol, ethanol, propanol, butanol, isopropanol and isobutanol, secondary butanols, n-pentanol and n-hexanol, methanol, ethanol and propanols being particularly suitable.

The molar ratio of the lactone of the formula II to the alkanol is advantageously from 1:0.5 to 1:10, in particular from 1:1 to 1:5.

The reaction is carried out at from 150° to 400° C., advantageously from 200° to 400° C., in particular from 250° to 400° C. As a rule, it is effected under from 0.1 to 100, in particular from 0.5 to 10, bar.

The reaction is carried out in the presence of an acidic catalyst. Examples of suitable catalysts are acidic oxides of elements of main groups three and four and of subgroups 4 to 6 of the periodic table, as well as protic and Lewis acids.

The reaction can be carried out by batchwise or continuously as a fixed bed reaction using fixed bed catalysts, for example by the liquid phase or trickle bed procedure, in the liquid phase or gas phase or by the fluidized bed method, or using fixed bed catalysts suspended in the liquid phase.

Examples of suitable acidic catalysts are heterogeneous catalysts, such as silica in the form of silica gel, kieselguhr or quartz, as well as titanium dioxide, zirconium dioxide, phosphorus pentoxide, vanadium pentoxide, boron trioxide, alumina, chromium oxides, molybdenum oxides, tungsten oxides and mixtures of these.

If lactones of the formula II are reacted over fixed bed catalysts of this type in the gas phase or by the fluidized bed method, a space velocity of from 0.1 to 10, in particular from 1 to 5, g of lactone of the formula II per g of catalyst per hour is advantageously maintained.

It is also possible to use, in the liquid phase, acidic catalysts dissolved to form a homogeneous solution. For example, mineral acids, such as sulfuric acid, phosphoric acid, hydrochloric acid, nitric acid or hydrobromic acid, and sulfonic acids, such as benzene sulfonic acid or p-toluenesulfonic acid, are suitable. The molar ratio of the lactone of the formula II to the mineral acid is, for example, from 1:0.001 to 1:1, in particular from 1:0.01 to 1:0.1.

The reaction of lactones of the formula II with alkanols in the liquid phase can be carried out, for example, by a method in which a mixture of the lactone of the formula II and the alkanol used is heated to the desired reaction temperature in the presence of a suspended fixed bed catalyst, as described above, or of a catalyst dissolved to form a homogeneous solution. When the reaction is complete, for example after from 0.5 to 5 hours, the reaction mixture is cooled and the acidic catalyst is removed, for example by filtration or neutralization. The reaction mixture is then advantageously subjected to fractional distillation to obtain the desired alkenecarboxylate.

In a preferred embodiment of the novel process in the gas phase or in the fluidized phase, for example, a mixture of a lactone of the formula II and the particular alkanol is first vaporized and then passed, with or without an inert gas, such as nitrogen, carbon dioxide or argon, in gaseous form, at the desired reaction temperature, over a fixed bed catalyst or a catalyst fluidized in an upward and downward direction. Silica, alumina, titanium dioxide, boron trioxide and mixtures of these have proven particularly useful for this purpose. The reacted mixture is condensed and then subjected to fractional distillation. Unconverted lactone of the formula II is advantageously recycled to the reaction.

The ω-alkenecarboxylates obtainable by the novel process are intermediates which have a wide range of uses. They are suitable, for example, for the preparation of ω-formylcarboxylates by hydroformylation. These are important starting compounds, for example for the preparation of aminocaproates and caprolactam.

The Examples which follow illustrate the process according to the invention.

EXAMPLE 1

A mixture of 8.3 g/hour of valerolactone and 2.7 g/hour of methanol (molar ratio 1:1) was pumped into an evaporator and passed from there, together with 3 l/h of nitrogen, over 5 g of an Al₂O₃ catalyst at 300° C. The gaseous reacted mixtures were condensed and weighed. The 192 g of discharged mixture collected after a reaction time of 20 hours were subjected to fractional distillation. This gave 40 g (21% of theory) of methyl 4-pentenoate, 4 g (2% of theory) of a mixture of 2- and 3-pentenoates and 76 g of unconverted valerolactone which contained 18% of 5-methylbutyrolactone (sum of lactones: 46% of theory).

EXAMPLE 2

10 ml/hour of a 50% strength by weight solution of 6-methylvalerolactone in methanol (molar ratio of methanol to lactone=3.6:1) were vaporized and passed, together with 3 l/h of nitrogen, over 10 g of alumina at a reaction temperature of 300° C.

The gaseous reacted mixture was condensed and subjected to a short path distillation under reduced pressure. After an experimental time of 50 hours, 330 g of crude product were isolated and were then subjected to fractional distillation.

In this way, 148 g (49% of theory) of methyl hexenoate (46% of 5-, 46% of 4-cis/trans- and 8% of 3- and 2-hexenoates) of boiling point 93°-97° C./150 mbar and 33 g (12% of theory) of unconverted 6-methylvalerolactone were obtained.

EXAMPLE 3

100 ml/hour of a 50% strength by weight solution of caprolactone in methanol (molar ratio of methanol to lactone=3.6:1) were vaporized at from 235° to 240° C. and passed, together with 30 l/h of nitrogen, over 50 g of alumina at a reaction temperature of 300° C.

The gaseous reacted mixture was condensed and subjected to a short path distillation under reduced pressure. After an experimental time of 20 h, 876 g of crude product were isolated in this way and were then subjected to fractional distillation.

In this way, 685 g (61% of theory) of methyl hexenoate (89% of 5-, 10% of 4-cis/trans- and 1% of 3- and 2-hexenoates) of boiling point 88°-91° C./150 mbar were obtained.

EXAMPLE 4

200 ml/hour of a 50% strength by weight solution of caprolactone in methanol (molar ratio of methanol to lactone=3.6:1) were vaporized at 300° C. and passed, together with 70 l/h of nitrogen, over 200 g (325 ml) of a fluidized alumina catalyst (particle size 0.1–0.3 mm; reaction temperature 300° C.).

The gaseous reacted mixture was condensed in cold traps over an experimental time of 8 hours and then subjected to fractional distillation under reduced pressure.

In this way, 595 g (70% of theory) of methyl hexenoate (33% of 5-, 65% of 4-cis/trans- and 2% of 3- and 2-hexenoates) of boiling point 95°-96° C./150 mbar were obtained.

We claim:

1. A process for the preparation of an alkenecarboxylate of the formula I

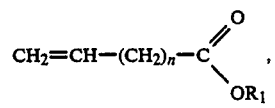

where $R_1$ is alkyl of 1 to 6 carbon atoms and n is 2, 3 or 4, which comprises reacting a lactone of the formula II

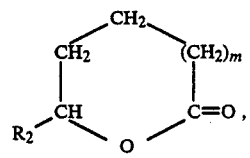

where $R_2$ is hydrogen or methyl and m is 1 or 2, with an alkanol of 1 to 6 carbon atoms in the presence of an acidic catalyst selected from the group consisting of acidic oxides of elements of the main groups three and four and of subgroups 4 to 6 of the periodic table, protic acids and Lewis acids at from 150° to 400° C.

2. The process of claim 1, wherein the lactone is caprolactone.

3. The process of claim 1, wherein the lactone is δ-valerolactone or 6-methylvalerolactone.

4. The process of claim 1, wherein silica, alumina, titanium dioxide, boron trioxide or a mixture of these is used as the acidic catalyst.

5. The process of claim 1, wherein a molar ratio of lactone of the formula II to alkanol of from 1:0.5 to 1:10 is maintained.

6. The process of claim 1, wherein the reaction is carried out in the gas phase.

7. The process of claim 6, wherein a space velocity of from 0.1 to 10 g of lactone of the formula II per g of catalyst per hour is maintained.

* * * * *